United States Patent
Jackson et al.

(10) Patent No.: US 11,549,879 B2
(45) Date of Patent: Jan. 10, 2023

(54) MEMBRANE INTEGRITY MONITORING IN WATER TREATMENT

(71) Applicant: HACH COMPANY, Loveland, CO (US)

(72) Inventors: Cary Burton Jackson, Fort Collins, CO (US); Richard Edward Leggett, Dickinson, TX (US)

(73) Assignee: HACH COMPANY, Loveland, CO (US)

( * ) Notice: Subject to any disclaimer, the term of this patent is extended or adjusted under 35 U.S.C. 154(b) by 290 days.

(21) Appl. No.: 16/614,898

(22) PCT Filed: May 18, 2018

(86) PCT No.: PCT/US2018/033316
§ 371 (c)(1),
(2) Date: Nov. 19, 2019

(87) PCT Pub. No.: WO2018/213662
PCT Pub. Date: Nov. 22, 2018

(65) Prior Publication Data
US 2020/0158618 A1 May 21, 2020

Related U.S. Application Data

(60) Provisional application No. 62/508,850, filed on May 19, 2017.

(51) Int. Cl.
*G01N 15/08* (2006.01)
*B01D 65/10* (2006.01)
(Continued)

(52) U.S. Cl.
CPC ........... *G01N 15/082* (2013.01); *B01D 65/10* (2013.01); *G01N 33/18* (2013.01); *G01N 15/02* (2013.01);
(Continued)

(58) Field of Classification Search
CPC .............................................. G01N 2015/084
See application file for complete search history.

(56) References Cited

U.S. PATENT DOCUMENTS

2004/0083798 A1  5/2004 Sadar
2012/0181014 A1  7/2012 Daussin et al.
(Continued)

FOREIGN PATENT DOCUMENTS

EP        0949947       10/1999
KR   20050063255 A  *  6/2005

OTHER PUBLICATIONS

English Translation of KR-20050063255-A (Year: 2005).*
(Continued)

*Primary Examiner* — Alexander A Mercado
(74) *Attorney, Agent, or Firm* — Ference & Associates LLC

(57) ABSTRACT

One embodiment provides a system, including: at least two water analyzers, wherein at least one of the at least two water analyzers is positioned upstream of a purification apparatus and wherein at least another of the at least two water analyzers is positioned downstream of the purification apparatus; at least one processor; and a memory device that stores instructions executable by the processor to: receive water analysis data from the at least two water analyzers, wherein the water analysis data comprises information related to membrane integrity; identify an algorithm for calculating membrane integrity based upon received data corresponding to system attributes; and calculate, using the identified algorithm, the membrane integrity based upon the received water analysis data. Other aspects are described and claimed.

18 Claims, 10 Drawing Sheets

(51) Int. Cl.
  *G01N 33/18* (2006.01)
  *G01N 15/02* (2006.01)
  *G01N 15/06* (2006.01)

(52) U.S. Cl.
  CPC ............... *G01N 2015/0693* (2013.01); *G01N 2015/084* (2013.01)

(56) References Cited

U.S. PATENT DOCUMENTS

| | | | |
|---|---|---|---|
| 2015/0000378 A1* | 1/2015 | Kent | E21B 33/0355 |
| | | | 73/38 |
| 2016/0231296 A1* | 8/2016 | Dressler | B01D 15/10 |
| 2016/0289090 A1 | 10/2016 | Liao et al. | |
| 2017/0189858 A1* | 7/2017 | Armgart | B01D 65/102 |
| 2018/0257040 A1* | 9/2018 | Powell | G01N 15/0826 |

OTHER PUBLICATIONS

International Searching Authority, Notification of Transmittal of the International Search Report and the Written Opinion of the International Searching Authority, or the Declaration, dated Aug. 31, 2018, pp. 13.

John D. Eisnor et al: "Evaluation of Particle Removal at Water Treatment Plants in Nova Scotia", Water Quality Research Journal of Canada, vol. 36, No. 1, Feb. 2001.

\* cited by examiner

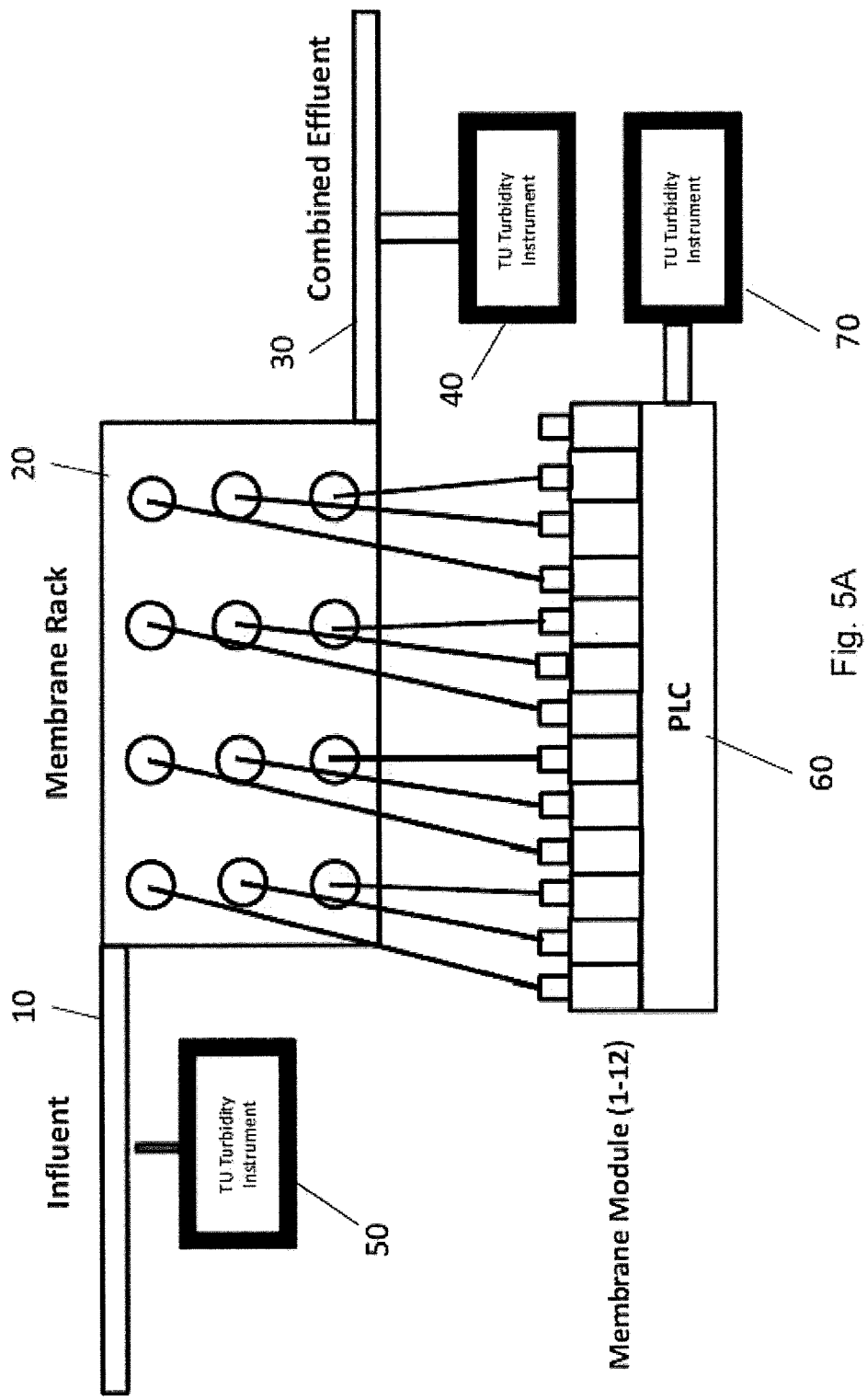

MEMBRANE INTEGRITY MONITORING IN WATER TREATMENT

FIELD

The present invention relates generally to water treatment, and, more particularly, to fast, real-time detection of water filtration quality, and membrane integrity.

BACKGROUND

Clean water is an important issue for communities and governments around the world. Facilities to clean water range in size from very small and rudimentary to large and complex. We are witnessing a trend of increased utilization of natural resources, society's increased usage of water, and rising levels of pollutants in water. While the demand for water is rising, the availability of clean sources of water is diminishing. Advances in water treatment can alleviate these issues.

One method for cleaning water is to use membranes (e.g., filters, etc.) to remove unwanted contaminants (e.g., particles, pathogens, heavy metals, etc.) in water. A current method of monitoring the effectiveness of membranes used for water treatment involves using a nephelometer to continuously measure turbidity, or other properties, of the water downstream from a filtering system. This form of measurement identifies the amount of undesired particles or pathogens that remain in the water after filtering through a group of filters on a filter rack. Thus, the measurement essentially measures whether the combined group of filters of the filter rack are performing as required, for example, as set by a regulatory agency.

BRIEF SUMMARY

In summary, one aspect provides a system, comprising: at least two water analyzers, wherein at least one of the at least two water analyzers is positioned upstream of a purification apparatus and wherein at least another of the at least two water analyzers is positioned downstream of the purification apparatus; at least one processor; and a memory device that stores instructions executable by the processor to: receive water analysis data from the at least two water analyzers, wherein the water analysis data comprises information related to membrane integrity; identify an algorithm for calculating membrane integrity based upon received data corresponding to system attributes; and calculate, using the identified algorithm, the membrane integrity based upon the received water analysis data.

Another aspect provides a method, comprising: receiving water analysis data from the at least two water analyzers, wherein the water analysis data comprises information related to membrane integrity; identifying an algorithm for calculating membrane integrity based upon received data corresponding to system attributes; and calculating, using the identified algorithm, the membrane integrity based upon the received water analysis data, wherein at least one of the at least two water analyzers is positioned upstream of a purification apparatus and wherein at least another of the at least two water analyzers is positioned downstream of the purification apparatus.

A further aspect provides an apparatus, comprising: at least one water purification apparatus; at least two water analyzers, wherein at least one of the at least two water analyzers is positioned upstream of the at least one water purification apparatus and wherein at least another of the at least two water analyzers is positioned downstream of the at least one water purification apparatus; at least one processor; and a memory device that stores instructions executable by the processor to: receive water analysis data from the at least two water analyzers, wherein the water analysis data comprises information related to membrane integrity; identify an algorithm for calculating membrane integrity based upon received data corresponding to system attributes; and calculate, using the identified algorithm, the membrane integrity based upon the received water analysis data.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

BRIEF DESCRIPTION OF THE SEVERAL VIEWS OF THE DRAWINGS

FIG. 5A is a structural diagram showing real-time direct membrane multiplex testing in an embodiment.

DETAILED DESCRIPTION

Figure 1:
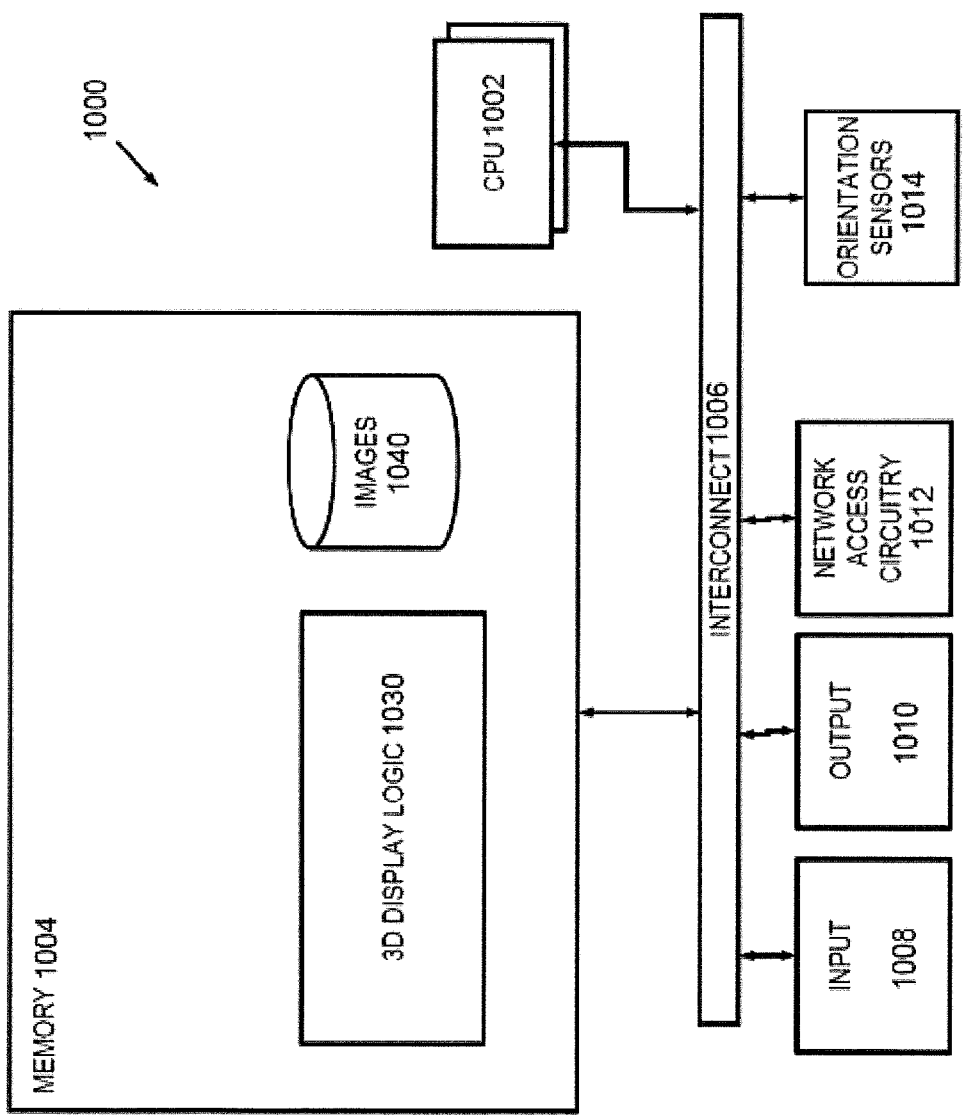
FIG. 1 is a block diagram showing an example apparatus device.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of example embodiments. One skilled in the relevant art will recognize, however, that various embodiments can be practiced without one or more of the specific details, or with other methods, components, materials, et cetera. In other instances, well-known structures, materials, or operations are not shown or described in detail. The following description is intended only by way of example, and simply illustrates certain example embodiments.

Conventional systems for measuring the effectiveness of filtering systems have low sensitivity and response, and cannot determine if a membrane or a filter is approaching failure in real-time. Additionally, when a failure becomes large enough to be detected using a conventional system, the filtration system may be severely damaged with many membranes or filters damaged. The operator must then take an entire filtration rack out of service costing time, money, and reducing the clean water output of the facility.

Additionally, because traditional techniques for measuring filtration effectiveness are not highly sensitive, operators have to take filtration racks out of service at predetermined intervals, typically once a day, to manually check the membranes and filters for defects or failures, for example, by performing a pressure test testing for membrane integrity. Taking the racks out of service is very costly and manually checking the membranes and filters is very time consuming. Thus, current methods to determine water filtration membrane effectiveness have many drawbacks. Typical filtration effectiveness methods use water analyzers to measure some parameter of the water, for example, nephelometers to measure turbidity, particle counters to measure organic carbon, total organic carbon analyzers to measure total organic carbon, and the like. Since the nephelometer may measure the parameter from a rack of membranes, and the effluent from each membrane is diluted by effluent from other membranes, an operator using traditional nephelometers cannot detect a membrane failure quickly enough or determine which membrane may have failed.

What is needed is a way for operators of water treatment facilities to have a way of detecting small changes in membrane integrity resulting from breached or degrading membranes such that problems may be detected quickly and subsequently corrected.

In accordance with the present invention, an embodiment provides a system and method for real time and fast detection of membrane breaches or degradation associated with water filtration. The system and methods as described herein provide a more accurate way to sense the quality of effluent or water attributes from a water filtration system including membrane integrity. For example, the system and operator may detect problems with the filtration system earlier due to the ability to detect small changes in membrane integrity over time. Additionally, the systems and methods as described herein provide a way to detect trouble with water filtration membranes at a time when a lower level of unwanted particles, pathogens, or other components are present in an effluent. Additionally, because the systems and methods as described herein can accurately identify when an unacceptable degradation or membrane breach has occurred, the membranes and/or filtration racks do not have to be taken completely out of service to inspect and correct an individual failed membrane module.

Referring to FIG. 1, a device 1000, for example, a device used as the viewing apparatus, is described. The device 1000 includes one or more microprocessors 1002 (collectively referred to as CPU 1002) that retrieve data and/or instructions from memory 1004 and execute retrieved instructions in a conventional manner. Memory 1004 can include any tangible computer readable media, e.g., persistent memory such as magnetic and/or optical disks, ROM, and PROM and volatile memory such as RAM.

CPU 1002 and memory 1004 are connected to one another through a conventional interconnect 1006, which is a bus in this illustrative embodiment and which connects CPU 1002 and memory 1004 to one or more input devices 1008 and/or output devices 1010, network access circuitry 1012, and orientation sensors 1014. Input devices 1008 can include, for example, a keyboard, a keypad, a touch-sensitive screen, a mouse, and a microphone. Output devices 1010 can include a display—such as a liquid crystal display (LCD)—and one or more loudspeakers. Network access circuitry 1012 sends and receives data through computer networks. Orientation sensors 1014 measure orientation of the device 1000 in three dimensions and report measured orientation through interconnect 1006 to CPU 1002. These orientation sensors may include, for example, an accelerometer, gyroscope, and the like, and may be used in identifying the position of the user.

Information handling device circuitry, as for example outlined in FIG. 1, may be used in devices such as water monitoring devices, filtration monitoring devices, water treatment facility equipment, tablets, smart phones, personal computer devices generally, and/or electronic devices which may be used in similar applications.

Figure 2A:
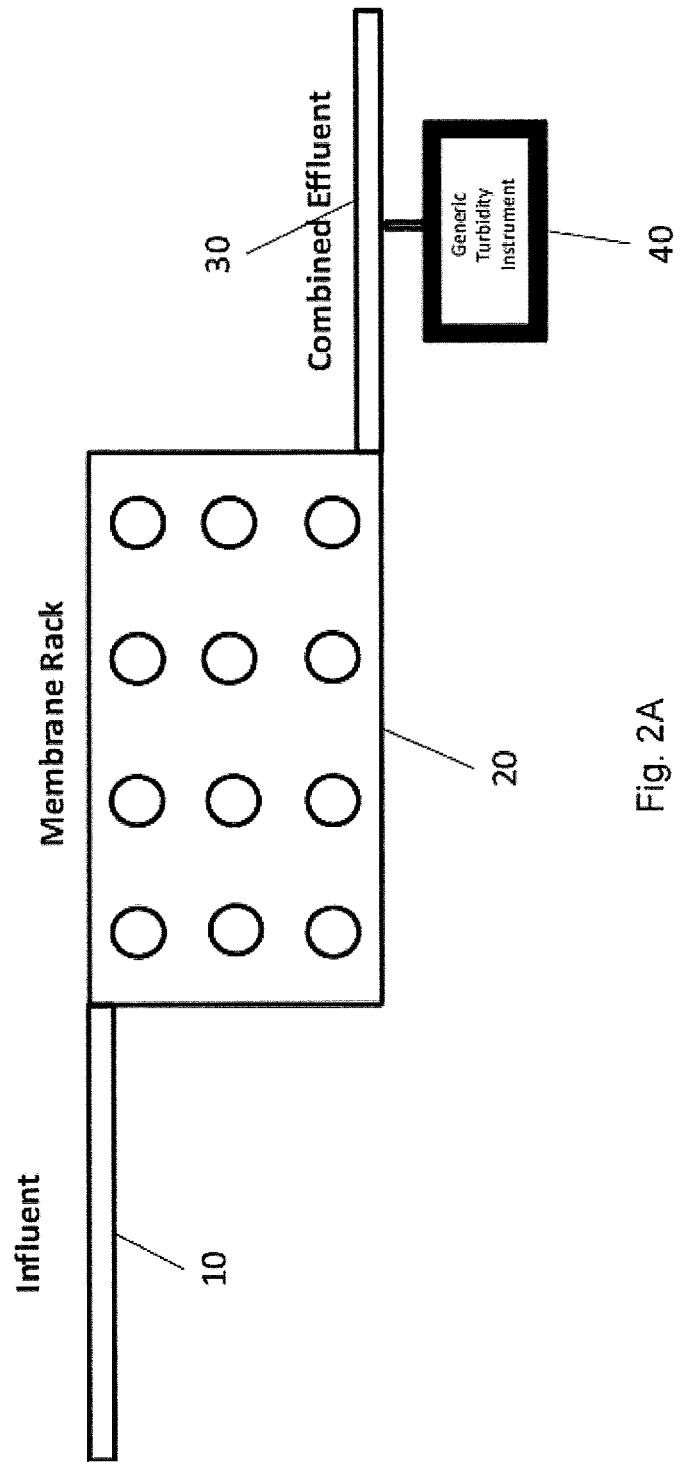
FIG. 2A is a schematic diagram showing a filtration monitoring system.
Figure 2B:
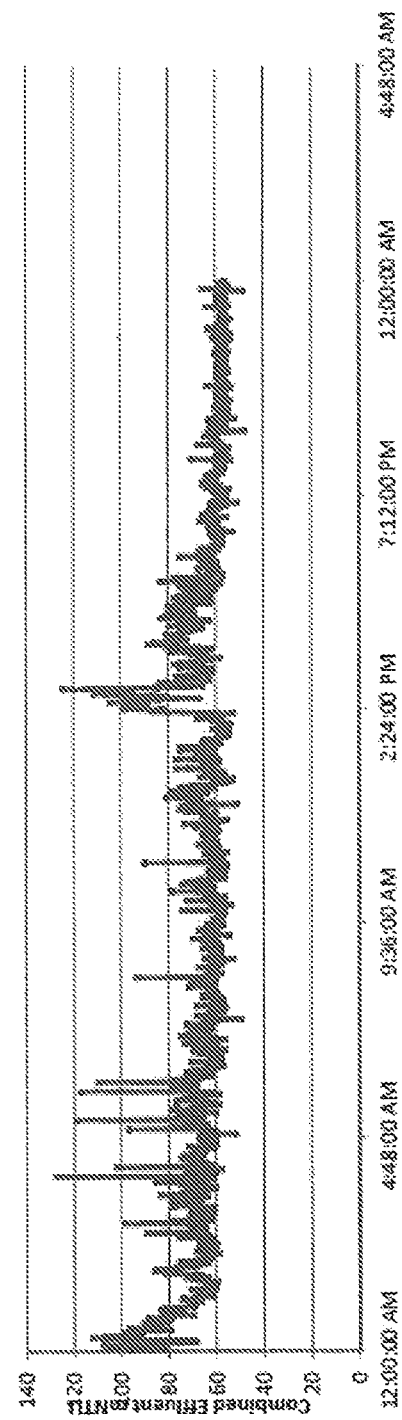
FIG. 2B illustrates a measurement of combined effluent, as measured in mNTU, over time from the turbidity instrument of FIG. 2A.

Referring now to FIG. 2A, a schematic of a membrane rack with influent (upstream) and combined effluent (downstream) flows is shown as an example system set-up used as an example herein. The set-up of the system as shown in FIG. 2A, is typical for conventional filtration monitoring systems. Fluid flows from the influent 10 to the filter rack 20 and then to the combined effluent 30. A generic turbidity instrument 40 may be located on the combined effluent flow. In this example, if the combined effluent equals or exceeds a measurement of 0.150 NTU for 15 minutes, it may signal that degradation of a membrane or a membrane breach has occurred. Accordingly, the membrane rack may be shut down and a pressure test may be performed to test membrane integrity. The chart in FIG. 2B illustrates a measurement of combined effluent, as measured in mNTU, over time from the generic turbidity instrument.

Figure 3:
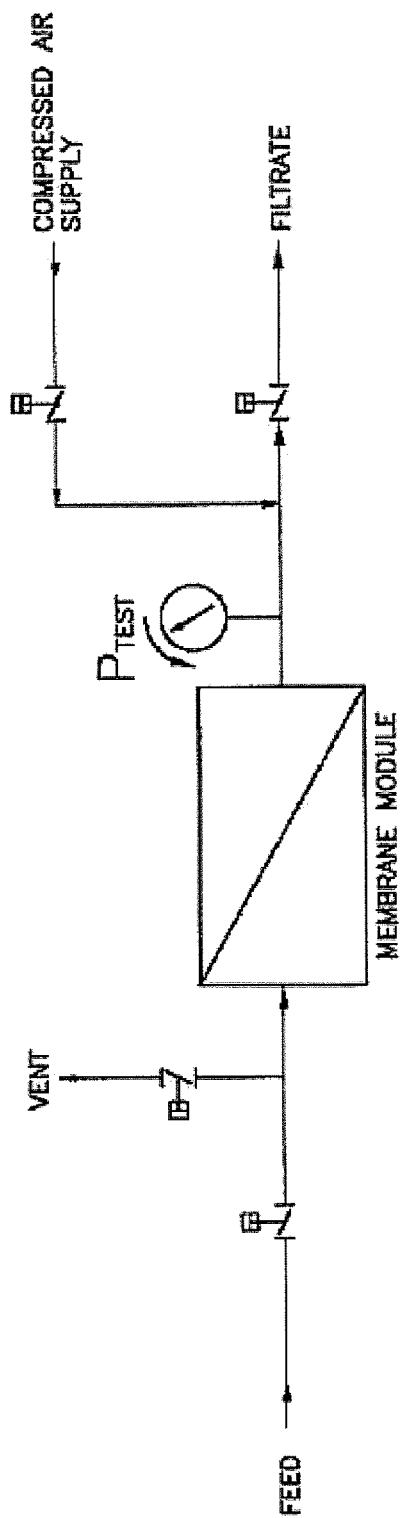
FIG. 3 is a structural diagram showing direct membrane integrity testing in an embodiment.

Referring now to FIG. 3, a schematic of a membrane rack with influent and combined effluent flows is shown as per the example used herein, again as per conventional techniques. In addition to the procedures performed as described above for FIG. 2, an off-line pressure decay test may be performed for the direct membrane integrity test. A schematic showing the membrane module undergoing a pressure test is illustrated. The pressure test may include placing the filter module in line with a feed and filtrate line, and associated vents, various valves, pressure gauge, and compressed air supply.

Spiral cellulose and hollow fiber membranes such as micro filtration (MF), ultrafiltration (UF), nanofiltration (NF), and reverse osmosis (RO) that are used in the treatment of water for indirect and direct potable use and reuse, require continuous membrane integrity monitoring and offline membrane decay pressure testing, as required by the United States Environmental Protection Agency (EPA) and State Regulators under the LT2 Enhanced Surface Water Treatment Rule. The testing results in the filters needing to be manually tested, using the pressure testing as described herein, periodically, typically once a day.

Traditionally, membrane integrity testing requires two approaches. The first approach includes indirect membrane integrity testing which requires a membrane filtration rack that consists of any number of membrane modules to have a nephelometer in place to continuously measure the turbidity of combined effluent or permeate of all the membrane modules on a continuous operating basis, or the per LT2 rule. When the turbidity of the combined effluent (clean drinking water) or permeate is determined to be 0.150 NTU or greater for a sustained period of 15 minutes, the membrane rack must be shut down from service and subjected to Direct Integrity Testing, as described above. Shutting down the rack costs the facility due to decreased output.

The Indirect membrane test is a turbidity threshold test based on nephelometry technology that is outdated and antiquated (greater than 20 years old). The turbidity measurement itself is a function of the dilution from the combined permeate of the membrane filters in a filtration rack. For example, there may be 20 filters in parallel, and contaminated breach water may contaminate the other effluent from properly working filters. Further, the threshold value of 0.150 NTU provides no information as to the membrane integrity performance as the turbidity of the feed water to the membrane rack is not measured, and the turbidity difference between the feed water and permeate is not determined.

Prior technology lacks sufficient sensitivity and response to provide early warning detection or real-time predictive, membrane breach. Traditional nephelometers (other than Hach TU nephelometers) cannot be used for this application. The nephelometers used to establish the 0.150 NTU threshold are based on turbidity events that have occurred 12 minutes to 15 minutes prior to the measurement using prior technology because of the effluent dilution, and travel time between the two nephelometers.

Therefore, traditionally the actual turbidity event is never measured in current or real-time. The consequences of this turbidity threshold approach using antiquated nephelometry event monitoring, increases the risk of undetected membrane breaches, that allows for possible fugitive pathogens, or undesirable contaminants, crossing the membrane filtration barrier and entering into the finished treated water. Therefore, using older technology, contaminants have already entered the finished water at the time of detection.

Direct membrane integrity testing requires the membrane filtration rack be taken out of production for membrane integrity evaluation, using pressure decay testing. If the pressure decay test fails, the membrane rack is taken out of service for maintenance and replacement of failed membrane modules. Time and resources may be wasted by taking the rack out of service. Additionally, because the indirect membrane integrity testing does not identify which membrane or group of membranes has failed, the entire rack needs to be taken out of service.

Direct membrane integrity testing is triggered by either: a) a turbidity that exceeds a threshold of 0.150 NTU for 15 minutes as normally obtained from the continuous indirect membrane integrity testing, or b) an integrity test must be conducted on each membrane unit at a frequency of no less than once each day the unit is in operation. Accordingly, direct membrane integrity testing is a significant pain point to the operation because it is labor intensive, requires the membrane rack be taken offline, thus increasing the overhead cost of water filtration.

Another type of filters, membrane biological reactor (MBR) filters, used in the treatment of water cannot be subjected to pressure decay testing, and therefore do not qualify for pathogen log removal disinfection credits. Without pathogen log removal disinfection credits, the water treatment process requires additional pathogen log removal credit technologies such as MF, UF, NR, and RO that increase the overall cost in water filtration. Log removal is a logarithmic removal (i.e. a factor of 100 denotes removal of 99% and results in a 2 log credit, a factor of 10 is a removal of 1). Filter systems may be tested for log removal by spiking the influent with a surrogate pathogen and measure the pathogen in the effluent. However, when the traditional systems are in use there is no process to measure the integrity of the membrane(s) in real-time. An embodiment uses a surrogate for log removal and allows real-time, in use integrity detection.

Figure 4A:
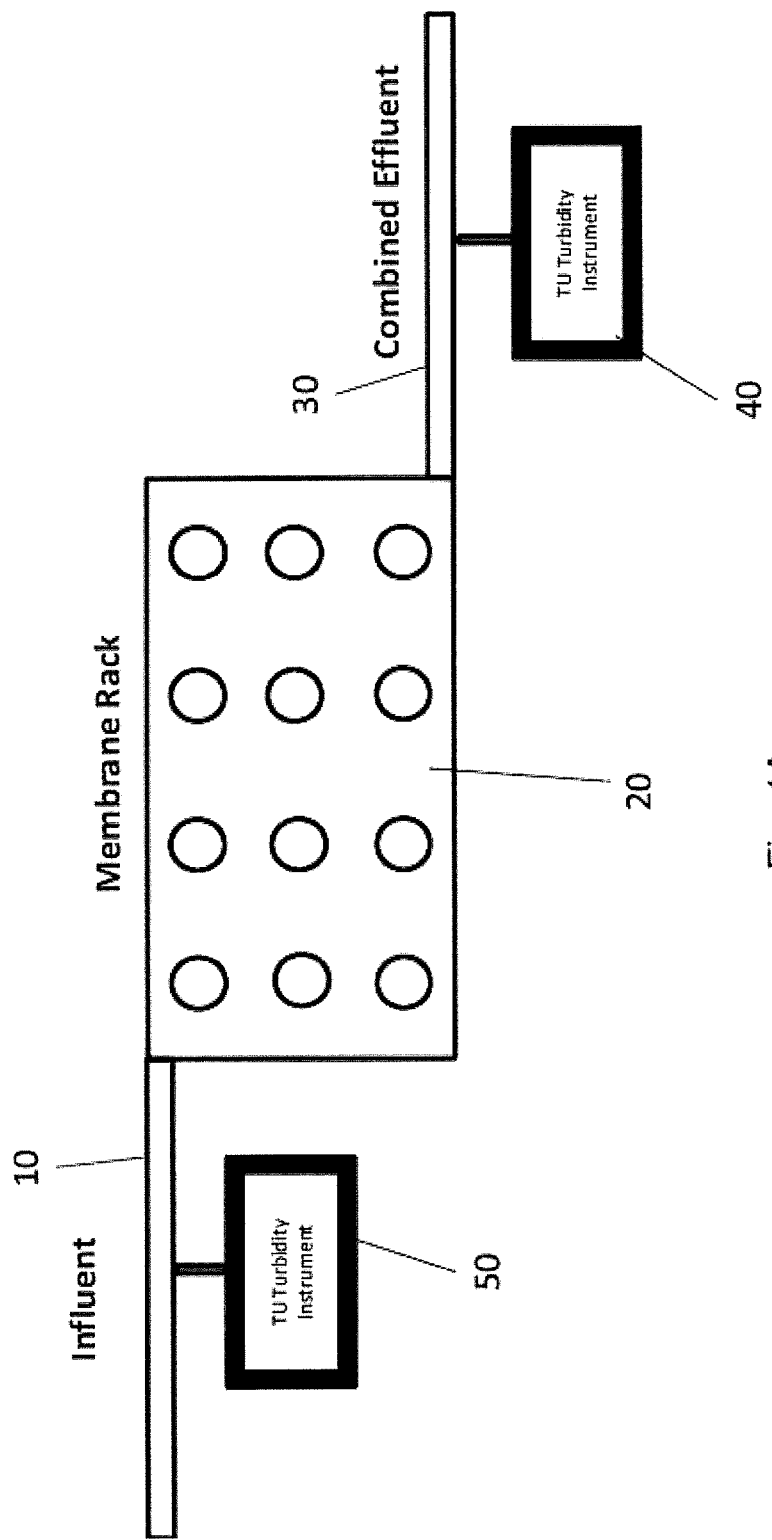
FIG. 4A is a schematic diagram showing an embodiment of a filtration monitoring system.

FIG. 4A illustrates a schematic of the filter rack with an influent and combined effluent flows as modified using embodiments of the systems and methods as described herein. Rather than having only single generic water analyzer 40 (e.g., nephelometer, turbidimeter, particle counter, etc.) as the effluent side of the system, as with conventional techniques, both the influent and combined effluent flows each contain an at least one associated nephelometer, which may include a high-sensitivity TU turbidimeter instrument, as described in more detail below. Thus, a first turbidimeter 40 measures the turbidity of the effluent stream 30 and a second turbidimeter 50 measures the turbidity of the influent stream 10. As shown in the equation below, $LR_{live}$ is the instantaneous log removal change as a function of time:

$$LR_{live} = \text{Log}_{10}\left(\frac{Inf_{ntu}}{Eff_{ntu}}\right)$$

Figure 4B:
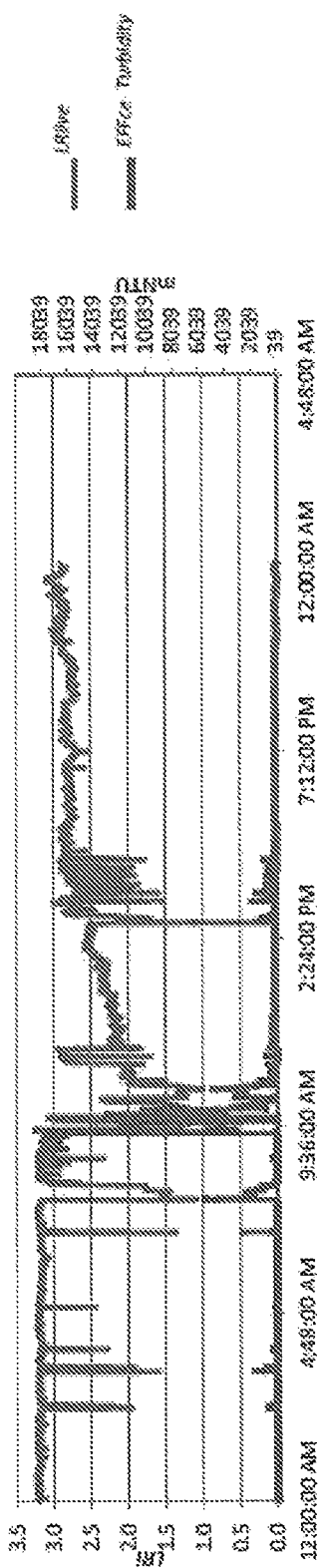
FIG. 4B illustrates a measurement of combined effluent, as measured in mNTU, over time from the turbidity instrument of FIG. 2A.

The $LR_{live}$ is equal to the log base 10 of the quotient of the turbidity measured in NTU of the influent divided by the turbidity of the effluent as measured in NTU. The chart in FIG. 4B shows $LR_{live}$ and EFFce turbidity plotted over time for the configuration shown in FIG. 4A. Thus, an embodiment provides a real time, on-line, and without filtration interruption method to identify membrane degradation, which may include a membrane breach.

FIG. 5A illustrates a schematic of the filter rack with an influent and combined effluent flows in an example embodiment. Both the influent and combined effluent flows each contain an at least one associated TU turbidity instrument. In an embodiment, a TU turbidity instrument may be associated with a single or groups of membranes. In embodiment, sampling system 60 can take an effluent sample from a given membrane or group of membranes and transport the sample to a third turbidimeter 70. This arrangement allows the system and operator to detect changes in membrane performance by measuring water attributes more quickly since turbidity measurement is correlated with one or a group of membrane unit(s). In other words, the operator can determine which membrane or groups of membranes is experiencing a change in membrane integrity, rather than having to test each membrane within the entire rack. As shown in the equation below, $LR_{live\ mm}$ is the instantaneous membrane integrity log removal of a specified membrane module.

$$LR_{live_{mm}} = \log\left(\frac{Inf_{ntu}}{Eff_{ntu_{mm}}}\right)$$

Figure 5B:
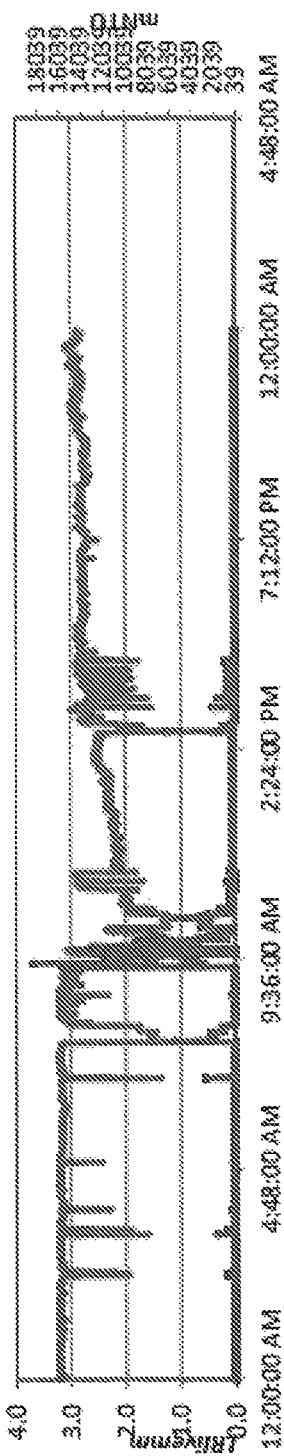
FIG. 5B illustrates a measurement of membrane integrity over time from the system of FIG. 5A.

The $LR_{live\ mm}$ is equal to the log of the quotient of the turbidity measured in NTU of the influent divided by the turbidity of the effluent as measured in $NTU_{mm}$. The chart in FIG. 5B shows $LR_{livemm}$ plotted over time for the configuration shown in FIG. 5A.

Figure 6A:
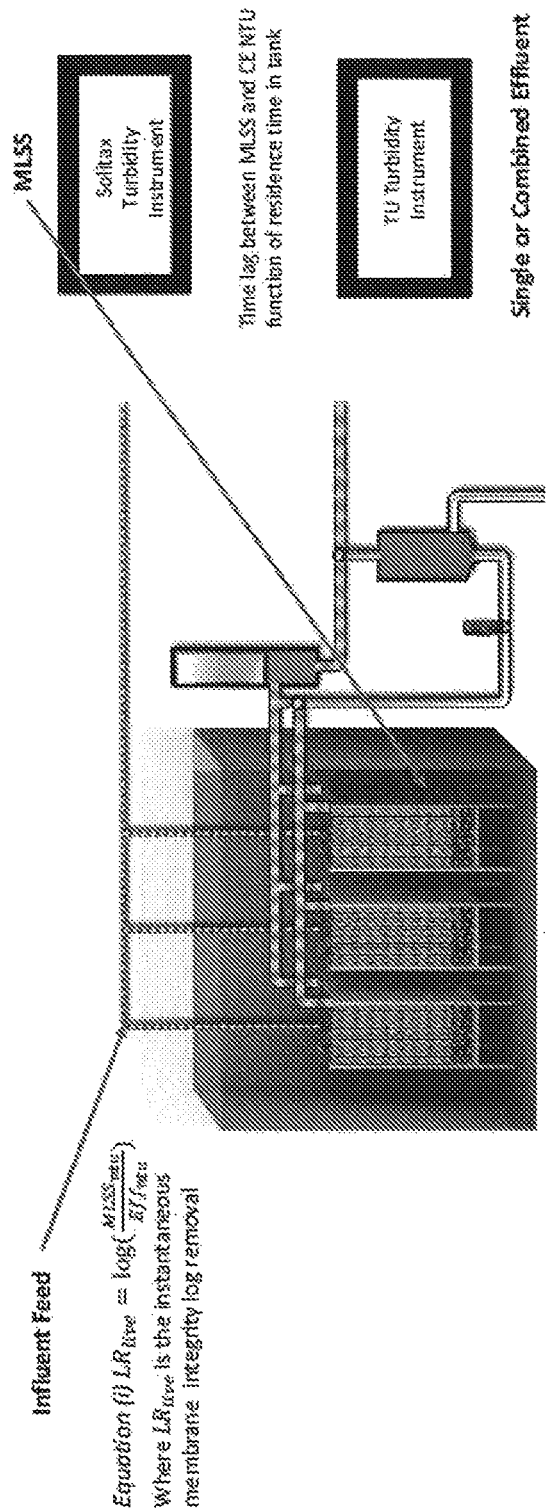
FIG. 6A is a structural diagram showing MBR direct membrane integrity testing in an embodiment.

FIG. 6A illustrates a schematic of membranes for filtration for an embodiment performing MBR direct membrane integrity testing. The system takes into account the time lag between mixed-liquor suspended solids (MLSS) and combined effluent as measured in NTU function of residence time in tank. Accordingly, an example algorithm for evaluating the membrane integrity is shown below.

Membrane Integrity Algorithm Definitions $LR_i$=Intrinsic log removal value (a constant) of the end user's membrane system being operated that was determined at the time the membrane system was known to be integral.

$LR_{live}$ = Log Removal change as a function of time

Residence Time in Filter = $t_2 - t_1$ $LR_{live} = \text{Log}_{10}\left(\frac{Inf_{t_1}}{Eff_{t_2}}\right)$ / Current live value of log removal $S = (LR_{live} - LR_i)$ / Difference between current performance and expected performance If $\frac{1}{\tau_1}\int_0^{\tau_1} S \cdot dt < 0$ (herinafter Equation (i)), then indication of filtration below LRi over a period τ1 (possible membrane failure)

Figure 6B:
FIG. 6B illustrates a measurement of membrane integrity over time from the system of FIG. 6A.

Boundary Condition: If $(10^{LR_i} \cdot Eff_{t_2}) < Inf_{t_1}$, then although log removal is lower than expected, it could be because the influent ($Inf_{NTU}$) is too low If $(10^{LR_i} \cdot Eff_{t_2}) > Inf_{t_1}$, then Equation (i) is relevant and indicates membrane failure Logic for Integrity Event Detection:

If $\left\{(10^{LR_i} \cdot Eff_{t_2} > Inf_{t_1})\text{And}\left(\frac{1}{\tau_1}\int_0^{\tau_1} S \cdot dt < 0\right)\right\}$ then integrity event/event To predict a membrane failure or degradation may be accomplished using time derivatives $$\left(\frac{dLR_{live}}{dt}\right)$$

and second derivatives $$\left(\frac{d^2 LR_{live}}{dt^2}\right)$$

which may be used to predict a membrane integrity event as in Control Theory. Filtering the turbidity signal may be necessary to eliminate minor turbidity events before the differentiations are applied. Regression analysis, often used in predictive systems, can also be used to find the current slope $$\left(\frac{dLR_{live}}{dt}\right)$$

of the recent turbidity measurements. The second differential $$\left(\frac{d^2 LR_{live}}{dt^2}\right)$$

can be used to gauge me slope change. FIG. 6B shows measurements of LRlive and EFFce for the configuration in FIG. 6A.

An embodiment uses at least one sensitive, rapid response turbidimeter, for example, the Hach TU5000 series turbidimeter or as a specific example the Hach TU5400. An embodiment uses an unpressurized testing method and a log removal threshold calculation approach, using two sensitive, rapid response time instruments that measure the membrane's performance and output nephelometric data. An embodiment uses at least one instrument measuring the upstream feed water and an at least one another instrument measuring the permeate of a filtration rack. Using these measurements, an embodiment calculates the current membrane integrity and predicts a future change in membrane integrity, degradation in the membrane, or catastrophic membrane breach. This unpressurized approach would not only provide other advantages as described herein, but also allow MBR filters, which if approved by regulators, to qualify for pathogen log removal disinfection credits.

In an embodiment the device is not restricted to the use of turbidity. Depending on the type of membrane filter or filters being used for water treatment, measurements from sensitive particle counting (particle enumeration and size), total carbon (inorganic and organic or total organic carbon), conductivity, or the like, may also serve to determine the membrane's performance, current membrane integrity status, and prediction of a catastrophic membrane breach. Additionally, a combination of the above devices and techniques may be employed simultaneously as inputs to an event monitoring device. Log removal may be applicable to detection of measurement of many types of contaminants listed herein. For example, pathogens such as cryptosporidium, a common drinking water contaminant and ~3 microns in size, may be detected by the system.

The water quality and measurements by the nephelometers may, in part, be based upon different system attributes. System attributes may include the type of filtration performed by the system, the flow of the system, the condition of the influent water, and the desired condition of the effluent water.

The example of a turbidimeter acting as the nephelometer will be used herein through for readability. However, as understood by one skilled in the art, different devices may be used, for example, nephelometers to measure turbidity, particle counters to measure organic carbon, and total organic carbon analyzers to measure total organic carbon. In an embodiment, at least one sensitive, rapid-response nephelometer may be placed on the influent side of a filter system, and another at least one sensitive, rapid-response or high-sensitivity nephelometer may be placed on the effluent (permeate) side of a filter system. In one embodiment, the influent and effluent instruments may be time-synchronized. In other words, the influent and effluent instruments may be calibrated so that they are measuring the same water when it enters the filtration rack and when it exits the filtration rack. As an example, if it takes 15 seconds for the water to flow through the filter rack, the system may be set so that the downstream nephelometer output is offset by 15 seconds as compared to the upstream nephelometer data. Such a time-synchronization allows the system to more accurately identify if the filtration rack is not performing as expected.

The turbidity of the influent and effluent over time may be measured at interval based on an operator's selected requirements. For example, the operator may indicate that measurements should be taken at 10 second intervals, minute intervals, and the like. To calculate the changes in the membrane system, the system may divide the influent measurement readings by effluent measurement readings and take the log of the quotient, and record and plot over time. Breaches to the membrane filter system may be quickly detected by measuring the live log removal change. Breaches may be identified due to identifying a smaller log quotient than expected or by identifying that the log quotient is trending in one direction. In other words, the slope of the change may predict a catastrophic or lesser failure of the membrane filter system, for example, clogs, small tears, and the like. Accordingly, the system may be used as a predictive indicator of membrane filter failure. Increasing the frequency of measurement increases the resolution of the data, and may lead to a faster detection of a failure event.

Accordingly, an embodiment combines current mandated indirect and direct integrity testing into one test that provides warning detection and prediction of membrane or filter degradation, including a membrane or filter breach, without requiring the membrane rack to be taken off line. This decreases maintenance and labor costs in membrane filtration and significantly ensures increased protection to consumers. Additionally, an embodiment provides a way that could be used by regulators to allow pathogen log removal disinfection credits for MBR filters.

An embodiment provides a continuously monitored metric which may be used for detecting and isolating a failed membrane module, a group of membrane modules, or a complete rack of membrane modules. In other words, the nephelometer, for example, the sensitive, rapid response turbidimeter, may measure effluent from a single membrane module, a group of membrane modules, or a complete rack or racks of membrane modules. Accordingly, the system may detect and isolate failed membrane modules. Upon detection of a membrane degradation, the system may take an action to reduce the possibility of contamination to the water. For example, the system may isolate the membrane or membrane group, shunt water, stop water flow to the membrane or group of membranes, stop the entire system, or the like.

An embodiment may be user programmed for the type of membrane in use. Although an embodiment may use a nephelometer to detect turbidity, other applications are disclosed. For example, filter modules for turbidity, sensitive particle counting (particle enumeration and size), total carbon (inorganic and organic or total organic carbon), conductivity, light-treatment, pathogens, ions, pH, sediment, silt, heavy metals, or the like may be used with the system. Therefore, the nephelometer may detect levels of many water attributes in addition to turbidity. In an embodiment, the analysis and predictability may be altered based upon the type of filter module, flow rates, the quality of influent water, desired quality of the effluent water, and the like. Upon detection of a change in membrane integrity, an embodiment may alert a processor and/or personnel on or offsite of the facility, and may also perform an additional action with respect to the system, as discussed above.

A number of components of the device 1000 are stored in memory 1004. In particular, 3D display logic 1030 is all or part of one or more computer processes executing within CPU 1002 from memory 1004 in this illustrative embodiment but can also be implemented, in whole or in part, using digital logic circuitry. As used herein, "logic" refers to (i) logic implemented as computer instructions and/or data within one or more computer processes and/or (ii) logic implemented in electronic circuitry. Images 1040 is data representing one or more images and/or views which may be stored in memory 1004.

This disclosure has been presented for purposes of illustration and description but is not intended to be exhaustive or limiting. Many modifications and variations will be apparent to those of ordinary skill in the art. The embodiments were chosen and described in order to explain principles and practical application, and to enable others of ordinary skill in the art to understand the disclosure for various embodiments with various modifications as are suited to the particular use contemplated.

Although illustrative embodiments have been described herein, it is to be understood that the embodiments are not limited to those precise embodiments, and that various other changes and modifications may be affected therein by one skilled in the art without departing form the scope or spirit of the disclosure.

What is claimed is:

1. A system, comprising:
   at least two water analyzers, wherein at least one of the at least two water analyzers is positioned upstream of a purification apparatus and wherein at least another of the at least two water analyzers is positioned downstream of the purification apparatus, wherein the purification apparatus comprises at least one membrane module;
   at least one processor; and
   a memory device that stores instructions that, when executed by the processor, cause the system to:
   receive water analysis data from the at least two water analyzers, wherein the water analysis data comprises information related to membrane integrity;
   identify, utilizing a log removal algorithm, a change in a membrane integrity of the at least one membrane module using received data from at least one upstream water analyzer and one of the at least one downstream water analyzer corresponding to system attributes, wherein the at least one upstream water analyzer and the at least one downstream water analyzer are time-synchronized based upon a time for a sample to travel from an upstream location to a downstream location, wherein the identifying comprises calculating, using the log removal algorithm and while the purification apparatus remains on-line and in service, a current log removal change based upon the received water analysis data and comparing the current log removal change with previous calculated log removal change values; and
   perform an action in response to an identified degradation, wherein the action comprises at least one of: shunting flow, notifying a user of the degradation, and shutting down the system.

2. The system of claim 1, wherein at least one of the at least two water analyzers comprises a turbidimeter.

3. The system of claim 1, wherein the water analysis data comprises at least one measurement of turbidity.

4. The system of claim 1, further comprising identifying, based upon the change in the membrane integrity, degradation of the purification apparatus.

5. The system of claim 4, wherein the purification apparatus comprises the at least one membrane module and wherein the degradation comprises a membrane breach.

6. The system of claim 1, further comprising predicting, based upon at least one time derivative, a degradation of the membrane integrity of the purification apparatus.

7. The system of claim 1, wherein the water analysis data is time-synced between the at least two water analyzers.

8. The system of claim 1, wherein the system attributes comprise measured upstream water attributes.

9. The system of claim 1, wherein the log removal algorithm of the at least one membrane module comprises identifying a relationship of the water analysis data and the log removal algorithm from the at least two water analyzers.

10. A method, comprising:
receiving water analysis data from the at least two water analyzers, wherein the water analysis data comprises information related to membrane integrity;
identifying, utilizing a log removal algorithm, a change in a membrane integrity of the at least one membrane module using received data from at least one upstream water analyzer and one of the at least one downstream water analyzer corresponding to system attributes, wherein the at least one upstream water analyzer and the at least one downstream water analyzer are time-synchronized based upon a time for a sample to travel from an upstream location to a downstream location, wherein the identifying comprises calculating, using the log removal algorithm and while the purification apparatus remains on-line and in service, a current log removal change based upon the received water analysis data and comparing the current log removal change with previous calculated log removal change values;
wherein at least one of the at least two water analyzers is positioned upstream of a purification apparatus and wherein at least another of the at least two water analyzers is positioned downstream of the purification apparatus, wherein the purification apparatus comprises at least one membrane module; and
performing an action in response to an identified degradation, wherein the action comprises at least one of: shunting flow, notifying a user of the degradation, and shutting down the system.

11. The method of claim 10, wherein at least one of the at least two water analyzers comprises a turbidimeter.

12. The method of claim 10, wherein the water analysis data comprises at least one measurement of turbidity.

13. The method of claim 10, further comprising identifying, based upon the change in the membrane integrity, degradation of the purification apparatus.

14. The method of claim 13, wherein the purification apparatus comprises the at least one membrane module and wherein the degradation comprises a membrane breach.

15. The system of claim 10, further comprising predicting, based upon at least one time derivative, a degradation of the membrane integrity of the purification apparatus.

16. The method of claim 10, wherein the water analysis data is time-synced between the at least two water analyzers.

17. The method of claim 10, wherein the log removal algorithm of the at least one membrane module comprises identifying a relationship of the water analysis data and the log removal algorithm from the at least two water analyzers.

18. An apparatus, comprising:
at least one water purification apparatus;
at least two water analyzers, wherein at least one of the at least two water analyzers is positioned upstream of the at least one water purification apparatus and wherein at least another of the at least two water analyzers is positioned downstream of the at least one water purification apparatus, wherein the purification apparatus comprises at least one membrane module, wherein at least one of the at least two water analyzers comprises a turbidimeter;
at least one processor; and
a memory device that stores instructions that, when executed by the processor, cause the system to:
receive water analysis data from the at least two water analyzers, wherein the water analysis data comprises information related to membrane integrity;
identify, utilizing a log removal algorithm, a change in a membrane integrity of the at least one membrane module using received data from at least one upstream water analyzer and one of the at least one downstream water analyzer corresponding to system attributes, wherein the at least one upstream water analyzer and the at least one downstream water analyzer are time-synchronized based upon a time for a sample to travel from an upstream location to a downstream location, wherein the identifying comprises calculating, using the log removal algorithm and while the purification apparatus remains on-line and in service, a current log removal change based upon the received water analysis data and comparing the current log removal change with previous calculated log removal change values; and
perform an action in response to an identified degradation, wherein the action comprises at least one of: shunting flow, notifying a user of the degradation, and shutting down the system.

* * * * *